United States Patent
Schulz et al.

(10) Patent No.: US 10,293,181 B2
(45) Date of Patent: May 21, 2019

(54) PROSPECTIVE ADAPTIVE RADIATION THERAPY PLANNING

(71) Applicant: KONINKLIJKE PHILIPS N.V., Eindhoven (NL)

(72) Inventors: Heinrich Schulz, Hamburg (DE);
Ingwer Carlsen, Hamburg (DE);
Rafael Wiemker, Kisdorf (DE);
Kirsten Meetz, Hamburg (DE);
Stewart Young, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 465 days.

(21) Appl. No.: 14/992,467

(22) Filed: Jan. 11, 2016

(65) Prior Publication Data

US 2016/0375268 A1 Dec. 29, 2016

Related U.S. Application Data (63) Continuation of application No. 13/055,761, filed as application No. PCT/IB2009/053187 on Jul. 22, 2009, now Pat. No. 9,262,590.
(Continued)

(51) Int. Cl.
*A61N 5/10* (2006.01)
*G16H 50/50* (2018.01)
(Continued)

(52) U.S. Cl.
CPC ............ *A61N 5/1039* (2013.01); *A61B 5/055* (2013.01); *A61B 6/032* (2013.01); *A61B 6/037* (2013.01);
(Continued)

(58) Field of Classification Search
CPC ............................... A61N 5/103; A61N 5/1039
See application file for complete search history.

(56) References Cited

U.S. PATENT DOCUMENTS

| 7,362,848 B2 | 4/2008 | Saracen |
| 7,574,251 B2 | 8/2009 | Lu |

(Continued)

FOREIGN PATENT DOCUMENTS

| WO | 2007014105 | 2/2007 |
| WO | 2007014106 | 2/2007 |

(Continued)

OTHER PUBLICATIONS

Kaus, M.R. "Automated 3D and 4D Organ Delineation for Radiation Therapy Planning in the Pelvic Area"; 2004; Proc. of SPIE—Int'l Soc. for Optical Engineering; vol. 5370:346-356.
(Continued)

*Primary Examiner* — Christine H Matthews (57) ABSTRACT

A therapy planner is configured to construct a therapy plan based on a planning image segmented into segments delineating features of a subject. A predictive plan adaptation module is configured to adjust the segments to represent a foreseeable change in the subject and to invoke the therapy planner to construct a therapy plan corresponding to the foreseeable change. A data storage stores a plurality of therapy plans generated for a subject by the therapy planner and the predictive plan adaptation module based on at least one planning image of the subject. A therapy plan selector is configured to select one of the plurality of therapy plans for use in a therapy session based on a preparatory image acquired preparatory to the therapy session.

20 Claims, 3 Drawing Sheets

Related U.S. Application Data

(60) Provisional application No. 61/088,737, filed on Aug. 14, 2008.

(51) Int. Cl.
*G06F 19/00* (2018.01)
*A61B 5/055* (2006.01)
*A61B 6/03* (2006.01)

(52) U.S. Cl.
CPC .............. *A61N 5/103* (2013.01); *G06F 19/00* (2013.01); *G06F 19/321* (2013.01); *G06F 19/3481* (2013.01); *G16H 50/50* (2018.01)

(56) References Cited

U.S. PATENT DOCUMENTS

| | | |
|---|---|---|
| 8,229,068 B2 | 7/2012 | Lu |
| 2004/0254448 A1 | 12/2004 | Amies |
| 2005/0201516 A1 | 9/2005 | Ruchala |
| 2006/0274885 A1 | 12/2006 | Wang |
| 2007/0076846 A1 | 4/2007 | Ruchala |
| 2007/0156453 A1 | 7/2007 | Frielinghaus |

FOREIGN PATENT DOCUMENTS

| | | |
|---|---|---|
| WO | 2007/133932 | 11/2007 |
| WO | 2008016795 | 2/2008 |

OTHER PUBLICATIONS

Keall, P.; "4-Dimensional Computed Tomography Imaging and Treatment Planning", 2004; Seminars in Radiation Oncology; 14(1)81-90.

PROSPECTIVE ADAPTIVE RADIATION THERAPY PLANNING

This is a continuation application of U.S. Ser. No. 13/055,761 filed Jan. 25, 2011 which is a national stage entry of PCT application no. PCT/IB2009/053187 filed Jul. 22, 2009 which claims the benefit of U.S. provisional application Ser. No. 61/088,737 filed Aug. 14, 2008, each of which is incorporated herein by reference in its entirety.

DESCRIPTION

The following relates to the medical arts, imaging arts, magnetic resonance arts, and related arts. It finds particular application in radiation therapy and is described with particular reference thereto.

In radiation therapy, spatially targeted dosages of ionizing radiation are applied to a tumor or other region containing cancerous or malignant tissue. Growing and rapidly multiplying cancer cells tend to be more susceptible to damage from ionizing radiation as compared with normal cells, and so enforced by the higher dosage administrated by proper planning the applied radiation preferentially kills cancerous or malignant tissue. Nonetheless, ionizing radiation is harmful to both malignant and healthy cells, and so precise spatial targeting of the radiation is important for applying effective radiation therapy to the malignancy while limiting collateral damage to healthy tissue. Damage to healthy tissue is also typically controlled by performing the radiation therapy in a series of sessions extending over several days, weeks, or months, with the expectation that radiation damage to healthy tissue may undergo healing during the time intervals between treatment sessions. This technique of distributing radiation therapy sessions over an extended period of time is sometimes referred to as fractionated radiation therapy, and each session is sometimes called a radiation therapy fraction.

In radiation therapy, the radiation beam is applied at angular positions around the subject in a manner that combines to produce a targeted total radiation dosage spatial distribution that is concentrated on the tumor or other region to be treated, while keeping the integrated exposure of certain radiation-sensitive critical organs below a safety threshold. Angular coverage can be achieved by using a plurality of stationary radiation sources distributed around the subject, or by revolving a single radiation source such as a linear accelerator (linac) around the subject (i.e., tomotherapy). The radiation therapy is planned in advance for a specific subject, based on imaging data acquired of that subject. Typically, computed tomography (CT) imaging is used for radiation therapy planning, although other imaging modalities such as magnetic resonance (MR) or positron emission tomography (PET) may also be utilized additionally to or instead of CT. The Brilliance™ Big Bore™ CT scanner (available from Koninklijke Philips Electronics N.V., Eindhoven, the Netherlands) is an illustrative CT scanner that is suitable for acquiring radiation therapy planning images. The Brilliance™ Big Bore™ CT scanner has an 85 cm patient aperture that is large enough to accommodate the patient arranged in typical radiation therapy positions.

To plan the radiation therapy session, the tumor or other target is delineated in the images, along with delineation of radiation-sensitive organs or regions whose radiation dosage must be limited. Computer simulations or other electronic calculations are used to optimize the radiation beam spatial profile and intensities to concentrate the radiation in the target while minimizing exposure of sensitive organs or regions, taking into account known information about radiation attenuation or absorption characteristics of the various tissues. One suitable radiation therapy planning system for performing such image guided radiation therapy is the Pinnacle™ radiation therapy planning system (available from Koninklijke Philips Electronics N.V., Eindhoven, the Netherlands). The radiation therapy planning process is computationally intensive, and a typical radiation therapy planning sequence can take a half-hour to several hours to perform.

The planning CT scanner or other planning imaging modality is typically physically separate from the linear accelerator (linac) or other radiation therapy system. Accordingly, the subject is imaged, followed by radiation therapy planning to generate the radiation therapy plan, followed by execution of the radiation therapy plan over an extended number of radiation therapy fractions or sessions. In view of the extended duration of the radiation therapy planning, it is generally not possible for both the planning imaging and the radiation therapy to be performed in a single session. Rather, the patient goes home, or to his or her hospital room, after the imaging, and returns at a later time for the first radiation therapy session. At the beginning of each radiation therapy session, the patient is positioned in the radiation therapy system in the same position (to the extent practicable) as in the imaging system and as in any previous radiation therapy sessions. In theory, this ensures that the radiation therapy plan remains valid throughout all of the radiation therapy sessions.

In practice, this optimistic view is often not satisfied. Even assuming that the patient is positioned in precisely the same way for the imaging and for each radiation therapy session, there remain many ways in which the anatomy can change between sessions. Internal organs can shift over time; bladders and other internal fluid receptacles empty or fill; stomach contents vary from session to session; gaseous bloating or gas pockets can form that change the anatomy; or so forth. Moreover, the tumor or other malignancy may shrink (a typical goal of radiation therapy) or enlarge (if the cancer continues to grow in spite of the radiation therapy or other treatment, or if the tumor enlarges due to radiation therapy-induced inflammation effects).

In existing radiation therapy techniques, there are two principle ways these anatomical changes are addressed. In one approach, no remedial action is taken at all. At best, the patient may be imaged before each radiation therapy session to verify that the patient is properly positioned and to verify that no prohibitively large-scale anatomic changes have taken place since the last session. If smaller scale changes have occurred, the physician or other medical personnel makes a judgment (possibly guided by objective clinical guidelines) as to whether it is safe and appropriate to perform the latest radiation therapy session in spite of the observed anatomical changes.

The other approach is to repeat the imaging and radiation therapy planning at intervals throughout the fractionated radiation therapy. Due to the length of the radiation therapy planning process, it is generally not practical to image the subject and immediately generate the radiation therapy plan. Instead, the patient must visit the imaging facility for each radiation therapy planning update, then go home or back to his or her hospital room to await the radiation therapy planning, and then to return for the next scheduled radiation therapy session. This is inconvenient and time-consuming for the patient, and the physician or other medical personnel also must spend considerable time in repeating the lengthy radiation therapy planning process.

Still further, the remediation provided by repeated radiation therapy planning is only partly effective. Repeating the radiation therapy planning can accommodate slowly occurring anatomical changes, such as tumor shrinkage over an extended period of time. However, repeated radiation therapy planning cannot correct for shorter term anatomical variations such as may occur in the time interval between the latest repetition of planning imaging and the next radiation therapy session. Short-term anatomical changes can occur due to changes in bladder levels, differing stomach contents, internal gaseous bloating, or so forth.

The following provides a new and improved apparatuses and methods which overcome the above-referenced problems and others.

In accordance with one disclosed aspect, a therapy method is disclosed, comprising: performing a therapy planning process to generate a plurality of therapy plans based on a planning image of a subject and one or more foreseeable changes in the subject; and performing a therapy session on the subject in accordance with a selected one of the plurality of therapy plans.

In accordance with another disclosed aspect, a digital storage medium is disclosed, which stores instructions executable in conjunction with a therapy delivery apparatus to perform the method recited in the immediately preceding paragraph.

In accordance with another disclosed aspect, a system is disclosed, comprising: a therapy planner configured to construct a therapy plan based on a planning image segmented into segments delineating features of a subject; a predictive plan adaptation module configured to adjust the segments to represent a foreseeable change in the subject and to invoke the therapy planner to construct a therapy plan corresponding to the foreseeable change; and a data storage for storing a plurality of therapy plans generated for a subject by the therapy planner and the predictive plan adaptation module based on at least one planning image of the subject.

In accordance with another disclosed aspect, a system is disclosed, comprising: a predictive plan adaptation module configured to generate a plurality of radiation therapy plans by applying a radiation therapy planner to (i) a planning image of a subject that is segmented into segments delineating a target feature to be irradiated and one or more critical features affecting radiation transmission or whose radiation exposure is to be constrained or limited and (ii) said planning image wherein said segments are adjusted to represent one or more foreseeable changes in the subject; and a radiation therapy plan selector configured to select one of the plurality of radiation therapy plans for use in a radiation therapy session based on a preparatory radiation therapy image acquired preparatory to the radiation therapy session.

One advantage resides in providing more accurate radiation therapy plans for fractionated radiation therapy.

Another advantage resides in accommodating changes in the subject that occur over the course of fractionated radiation therapy.

Another advantage resides in computationally efficient predictive adaptation of the radiation therapy plan to foreseeable changes in the subject.

Further advantages will be apparent to those of ordinary skill in the art upon reading and understand the following detailed description.

Figure 1:
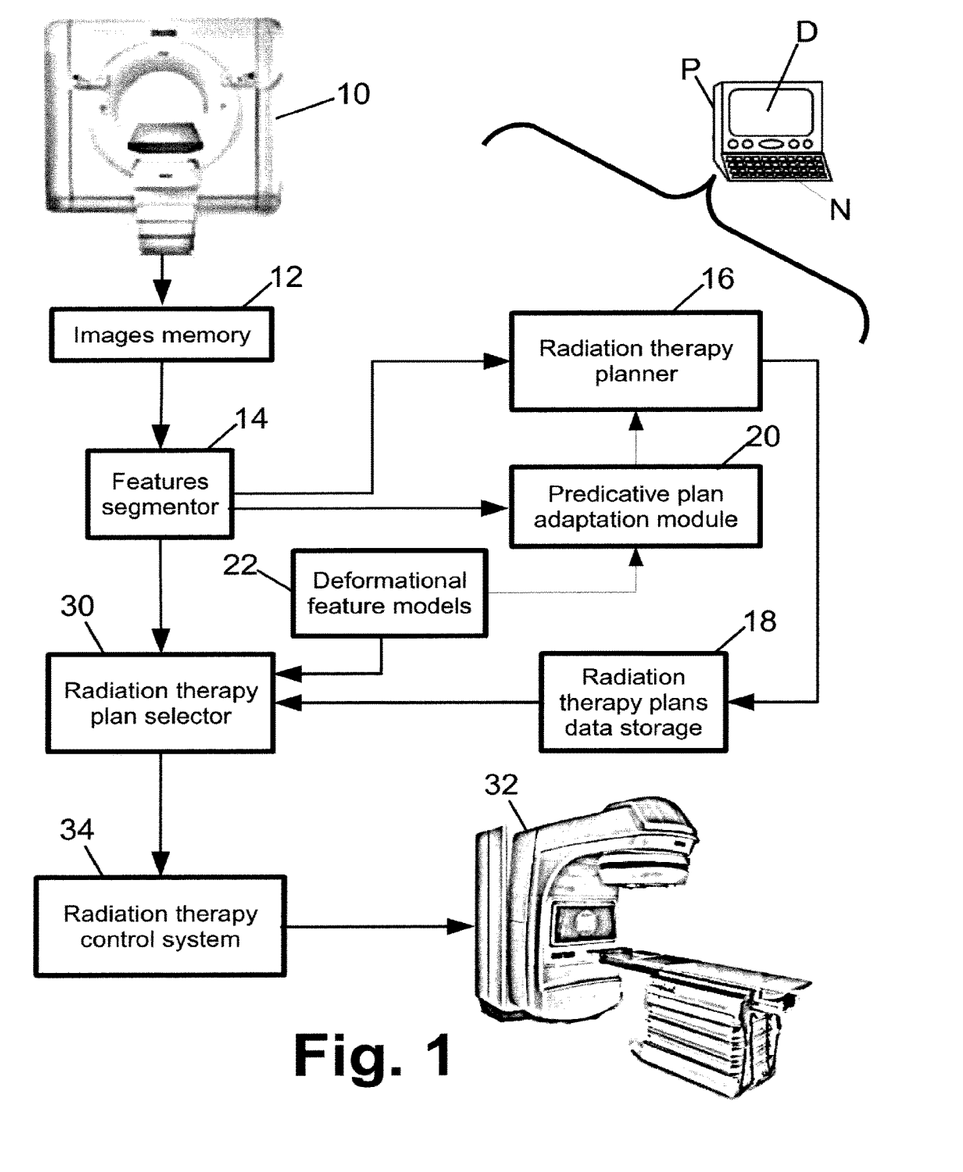
FIG. 1 diagrammatically shows a fractionated radiation therapy system.

With reference to FIG. 1, a radiation therapy system includes an imaging modality 10 suitable for acquiring planning images for planning the radiation therapy. In some embodiments, the imaging modality 10 is a computed tomography (CT) scanner, such as the Brilliance™ Big Bore™ CT scanner (available from Koninklijke Philips Electronics N.V., Eindhoven, the Netherlands). Other CT scanners can be used, as well as other imaging modalities such as positron emission tomography (PET), magnetic resonance (MR), single photon emission computed tomography (SPECT), or so forth. In some regulatory jurisdictions, the use of CT is a mandatory component of radiation therapy planning. The imaging modality 10 can also be a plurality of different imaging modalities, such as CT and PET, embodied as independent scanners or as a hybrid scanner, such as a hybrid SPECT/CT scanner.

Acquired images are stored in an images memory 12, and are segmented by a features segmentor 14 to identify segments delineating a target feature to be irradiated and one or more critical features affecting radiation transmission or whose radiation exposure is to be constrained or limited. As used herein, the term "critical feature" denotes any anatomical feature affecting radiation transmission or whose radiation exposure is to be constrained or limited. For example, the target feature to be irradiated may be a cancerous tumor or other malignancy, and the one or more critical features may include for example the heart, lungs, or other radiation-sensitive internal organs, or a metal implant that affects (in this case, blocks) radiation transmission. As used herein, the term "segmentation" and similar terms refers to any algorithm, technique, or user interfacing device or system that delineates the target feature and that delineates critical organs affecting radiation transmission or whose radiation exposure is to be controlled or limited. The segmentation may be partially or wholly automated by employing algorithms that identify relevant regions in the image based on image characteristics such as edges, connected groupings of pixels or voxels of similar intensity or grayscale level, or so forth. The segmentation may be partially or wholly manual, for example providing a user interface displaying slices of the image on which medical personnel can use a mouse pointer or the like to identify and delineate the target feature and neighboring critical features. Semi-automated segmentation techniques that combine automated algorithms with manual adjustment or input are also contemplated. The features segmentor 14 may be embodied, for example, by a computer or other digital processor P including or operatively connected with a suitable display D for displaying image slices or renderings and one or more user input devices N such as a keyboard, mouse, trackball, trackpad, touch-sensitive screen, or the like enabling user input for defining or adjusting feature-delineating segments.

A radiation therapy planner 16 receives the planning image segmented into segments delineating a target feature to be irradiated and one or more critical features affecting radiation transmission or whose radiation exposure is to be constrained or limited, and constructs a radiation therapy plan based on the segmented planning image along with radiation attenuation or absorption information pertaining to tissues of the segments, quantitative specifications as to the integrated radiation dose to be delivered to the target feature to be irradiated and as to quantitative constraints or limits on the radiation exposure of critical features whose radiation exposure is to be constrained or limited, and optionally other information relevant to constructing the radiation therapy plan. In some embodiments, the radiation therapy planner 16 is suitably embodied as the computer or other processor P executing software defining the Pinnacle™ radiation therapy planning system (available from Koninklijke Philips Electronics N.V., Eindhoven, the Netherlands).

Generation of a radiation therapy plan from the segmented planning image or images is a computationally intensive process. In some embodiments, the radiation therapy planner 16 may take a half-hour to ten hours or longer to generate the radiation therapy plan from the segmented planning image or images. The radiation therapy plan generated by the radiation therapy planner 16 from the segmented planning image is referred to herein as a base radiation therapy plan, and the base radiation therapy plan is stored in a radiation therapy plans data storage 18 for later usage to control a radiation therapy session. The base radiation therapy plan is suitable for performing a radiation therapy session on the subject as long as no significant change occurs in the subject in the interim between acquisition of the planning image or images and performance of the radiation therapy session.

However, in practice some changes may occur in the time between acquiring the planning image or images and performance of the radiation therapy session. Moreover, fractionated radiation therapy includes a succession of radiation therapy sessions performed over an extended period of time, possibly spanning days, weeks, months, or longer, which further increases a likelihood of the subject manifesting a change at some point during the course of the fractionated radiation therapy. The term "anatomical change" as used herein encompasses any change to the subject anatomy that may affect the radiation therapy. Anatomical changes include, for example: changes in the size or geometry of anatomical features such as tumor growth or shinkage, bladder filling or emptying, or so forth; changes in the radiation absorption or attenuation characteristics of a feature due to changes in the density of tissue comprising the feature; or addition or removal of anatomical features due to surgical operations such as insertion of a metal plate or the like, surgical removal of an organ such as the appendix, or so forth. More generally, the term "change in the subject" encompasses any change that may affect the therapy, and encompasses anatomical changes as well as other relevant changes in the subject such as partial necrosis of a tumor.

Changes in the subject could be accounted for by acquiring a new planning image or images manifesting the change using the imaging modality 10, and applying the radiation therapy planner 16 to generate a new radiation therapy plan that accommodates the change. However, this approach is untenable in many situations, such as when the change is detected via a preparatory image acquired shortly before commencement of the radiation therapy session, or when repeated imaging is cost-prohibitive, or when the change in the subject is large enough to affect the radiation therapy but too small to justify repetition of the radiation therapy planning.

Accordingly, the radiation therapy system of FIG. 1 includes a predictive plan adaptation module 20, which operates in conjunction with a deformational feature models 22 to deform or otherwise adjust at least one segment of the segmented planning image or images to represent a foreseeable change in the subject. The predictive plan adaptation module 20 then invokes the radiation therapy planner 16 respective to the adjusted segmented planning image or images in order to generate a predictive adapted radiation therapy plan that is appropriate for use if the foreseeable change actually occurs. The predictive adapted radiation therapy plan is stored in the radiation therapy plans data storage 18, and this process can optionally be repeated a plurality of times to generate a plurality of predictive adapted radiation therapy plan appropriate for a corresponding plurality of different foreseeable changes in the subject. The term "foreseeable change" as used herein refers to any change in the subject that is considered sufficiently likely to occur in the subject to justify generating a predictive adapted radiation therapy plan appropriate for the change.

Some illustrative examples of foreseeable anatomical changes include: varying degrees of shrinkage of a tumor or other target feature to be irradiated (foreseeable since the goal of fractionated radiation therapy is gradual shrinkage of the tumor over a series of radiation therapy sessions); varying degrees of growth of a tumor or other target feature to be irradiated (foreseeable since radiation therapy and other oncological treatments are not always wholly successful, and it may be foreseeable that the tumor may grow in spite of radiation therapy or other oncological treatment); varying sizes of internal bladders (foreseeable since bladder size varies with the amount of fluid contained); translational and/or rotational movement of certain critical organs that are known to have variable positions; and so forth. Other foreseeable changes may include, for example, necrosis of a tumor or tumor portion responsive to oncological therapy (foreseeable since this is a goal of the radiation therapy).

The result of operation of the radiation therapy planner 16 and the predictive plan adaptation module 20 is the generation of a plurality of radiation therapy plans stored in the radiation therapy plans storage 18. The base radiation therapy plan is suitable if the subject is substantially unchanged compared with the subject at the time the planning image or images were acquired. The various predictive adapted radiation therapy plans are suitable if the subject changes in a foreseen way corresponding to the predictive adapted radiation therapy plan.

At commencement of a radiation therapy session, a suitable effort is made to ascertain the state of the subject. In some embodiments, a preparatory image of the subject is acquired shortly before (for example, on the same day as, and preferably within an hour or a few hours before) applying therapeutic radiation. The preparatory image of the subject can be acquired using the same imaging apparatus 10 as was used to acquire the planning image or images, or can use a different imaging apparatus. In some contemplated embodiments, the preparatory image is a cone beam CT image acquired using a CT gantry including a kilovolt x-ray source and x-ray detector mounted together with or otherwise integrated with the device that delivers the therapeutic radiation. The acquired preparatory image is suitably segmented by the features segmentor 14 to identify up-to-date segments delineating the target feature to be irradiated and the one or more critical features affecting radiation transmission or whose radiation exposure is to be constrained or limited. Comparison of these segments with corresponding segments of the segmented planning image enables determination of changes in the geometry of a feature, or changes in density of a feature (and hence, a corresponding change in the radiation absorption or transmission characteristic of the feature), or removal of a feature by surgery or other means, or a functional change such as a regional necrosis detectable in the case of functional imaging, or other changes.

A radiation therapy plan selector 30 selects the most appropriate radiation therapy plan from amongst the plurality of radiation therapy plans stored in the radiation therapy plans data storage 18 based on changes (if any) identified based on the preparatory image of the subject. For example, if no significant changes are identified, then the base radiation therapy plan is suitably selected. On the other hand, if the preparatory image indicates substantial shrinkage or growth of the tumor, the predictive adapted radiation therapy plan most closely corresponding to the up-to-date extent of tumor shrinkage or growth is selected. Identified changes in critical features can likewise be accommodated by using the predictive adapted radiation therapy plan most closely corresponding to the up-to-date state of the critical features.

A preparatory image is a suitable tool for identifying most changes relevant to the radiation therapy; however, other approaches can be used to identify changes in the subject. For example, other oncological diagnostic or monitoring techniques may be used to detect growth or shrinkage of the tumor. Surgical removal of a critical feature such as a radiation-blocking metallic implant may be identified in tautological fashion based on knowledge of the surgical removal. Bladder extension may be estimated based on fluid retention measurements. The radiation therapy plan selector 30 can select the most appropriate radiation therapy plan based on these change identifications instead of or in addition to based on a preparatory image or images.

Because the various predictive adapted radiation therapy plans are generated based on foreseeable changes in the subject, these various predictive adapted radiation therapy plans can be generated by the radiation therapy planner 16 at the invocation of the predictive plan adaptation module 20 well before commencement of any radiation therapy session. Because of this, the various predictive adapted radiation therapy plans can be, and preferably are, available at commencement of the radiation therapy plan. As a result, operation of the radiation therapy plan selector 30 introduces little or no delay into the radiation therapy session. That is, if a foreseen change is identified using the preparatory image or another tool, the radiation therapy plan selector 30 selects the relevant predictive adapted radiation therapy plan, which already exists.

Once the radiation therapy plan selector 30 selects the most appropriate radiation therapy plan, a suitable apparatus 32 for delivering therapeutic radiation is controlled by a suitable radiation therapy control system 34 to deliver the therapeutic radiation in accordance with the selected most appropriate radiation therapy plan. For example, in the illustrated embodiment the radiation therapy delivery apparatus 32 is a tomographic linear accelerator (linac), and the radiation therapy control system 34 operates multileaf collimator (MLC) or other radiation beam profile-shaping apparatus of the linac 32 to modulate beam intensity and profile as the linear accelerator is revolved around the subject, so as to deliver a radiation dose distribution into the subject that provides the desired integrated radiation dosage to the target feature while suitably limiting or constraining radiation exposure of sensitive critical features.

The various modules and other computational components 14, 16, 20, 30, 34 of the radiation therapy system can be variously embodied by a single digital processor, a two or more digital processors, computers, application-specific integrated circuitry (ASIC), or so forth. For example, the illustrated computer P can embody all the computational components 14, 16, 20, 30, 34, or a first instance of the computer can embody the imaging- and planning-related computational components 14, 16, 20 while a second instance of the computer can embody the radiation-therapy session-related computational components 30, 34, or so forth. Similarly, the data storage components 12, 18, 22 can be variously embodied as various instances or combinations of instances of random access memory (RAM), read-only memory (ROM), magnetic storage media (e.g., a magnetic disk or computer hard drive or the like), optical storage media (e.g., a CD, DVD, or other an optical disk), electrostatic storage media (e.g., a FLASH memory), or so forth.

Figure 2:
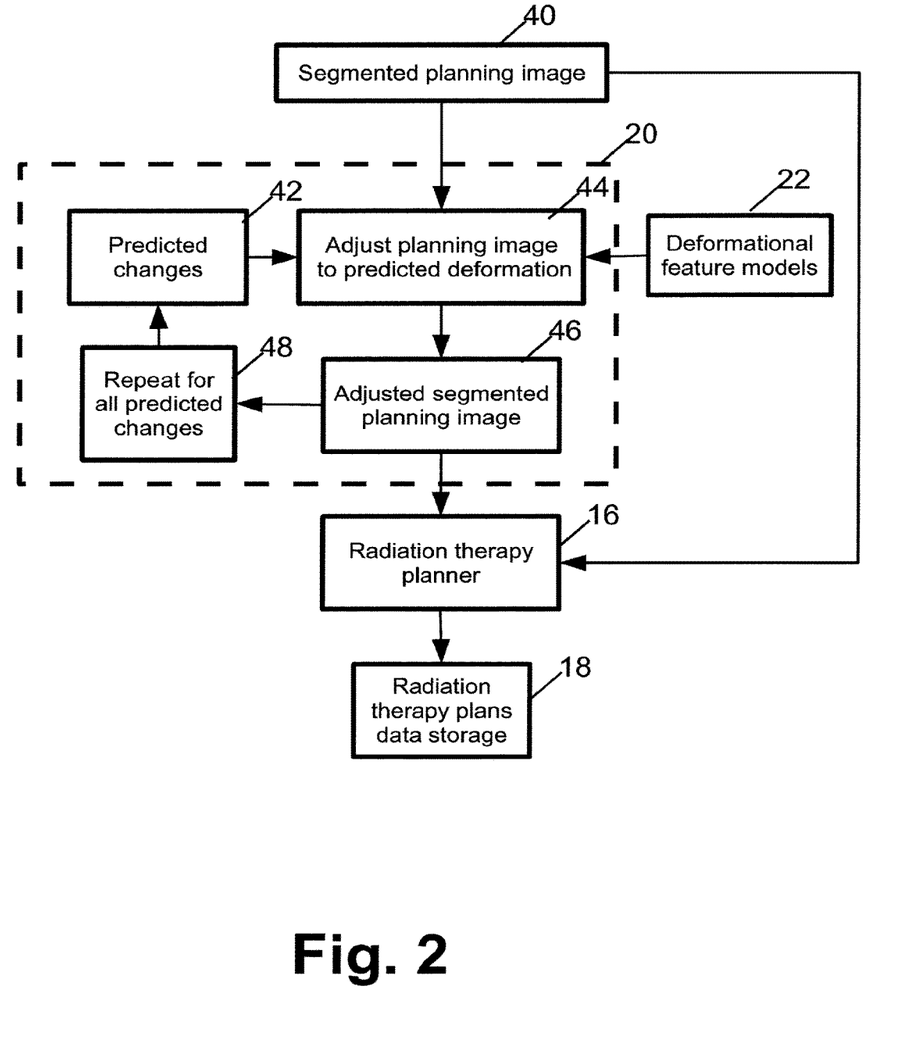
FIG. 2 diagrammatically shows a method for generation of a plurality of predictive adapted radiation therapy plans using the system of FIG. 1.

With reference to FIG. 2, operation of the radiation therapy planner 16 and the predictive plan adaptation module 20 is further described. The planning image in segmented form 40 (that is, after segmentation by the features segmentor 14) is input to the radiation therapy planner 16 to generate the base radiation therapy plan, which is stored in the radiation therapy plans data storage 18.

The segmented planning image 40 is also input to the predictive plan adaptation module 20. This module 20 identifies predicted changes 42, which may be stored in an internal storage of the predictive plan adaptation module 20, or may be input to the predictive plan adaptation module 20 by a user (for example, via the one or more user input devices N), or so forth. For example, the predicted changes 42 may be stored as a set of foreseen percentage or fractional changes in the average diameter of a generally spherical tumor, or as a series of sizes and shapes for a fluid bladder.

For a first one of the predicted changes 42, the segments of the segmented planning image 40 is or are adjusted to the predicted deformation or deformations (or density change or changes or other change or changes) in a computational operation 44. For geometric anatomical changes, such as tumor shrinkage or growth, organ movement, size, or shape changes, or so forth, the deformational operation 44 optionally utilizes the deformational feature models 22 to model the foreseen geometric anatomical change. In some cases, a single foreseen anatomical change may entail deformation of two or more segments. For example, the predicted anatomical change corresponding to shrinkage of a tumor pressing against the right lung may include both reduction in the size of the segment delineating the tumor and increase in the size of, and possibly change in the shape of, the segment delineating the right lung. Changes in tissue density of a segment may be accounted for by adjusting the radiation attenuation or absorption of the segment. Partial necrosis of the tumor may be accounted for by reducing the target region of the radiation therapy to exclude the necrotized portion of the tumor.

The output of the predicted change operation 44 is an adjusted segmented planning image 46, which is then input to the radiation therapy planner 16 to generate the predictive adapted radiation therapy plan that is also stored in the radiation therapy plans data storage 18. A looping, iteration, or other sequential processing operation 48 causes the predictive plan adaptation module 20 to successively apply the predicted change operation 44 and invocation of the radiation therapy planner 16 to generate a different predictive adapted radiation therapy plan for each of the predicted changes 42.

In this process, the radiation therapy planner 16 is invoked to generate a different radiation therapy plan for each foreseen change in the subject. In some embodiments, each different radiation therapy plan is generated independently, that is, without reference to the other generated radiation therapy plans. However, it will be appreciated that the foreseen changes in the subject are typically relatively small. For example, the predictive adapted radiation therapy plan corresponding to a 10% shrinkage of the tumor is expected to be relatively similar to, albeit not identical with, the base radiation therapy plan.

Accordingly, the radiation therapy planner 16 may optionally utilize information from previously generated radiation therapy plans in producing later radiation therapy plans. For example, in some embodiments the radiation therapy planner 16 operates iteratively starting from a set of initial parameter values (for example, MLC parameters as a function of tomographic position) to generate final optimized parameter values. For example, consider an illustrative example in which a base radiation therapy plan is to be generated, along with additional predictive adapted radiation therapy plans for each of the following foreseen tumor shrinkage levels: 10%, 30%, 50%, and 80% shrinkage. In this illustrative example, a suitable approach is to first generate the base radiation therapy plan. Then, the predictive adapted radiation therapy plan is suitably generated for the foreseen 10% shrinkage using the optimized parameters of the base radiation therapy plan as the initial parameter values for the optimization. Then, the the predictive adapted radiation therapy plan is suitably generated for the foreseen 20% shrinkage using the optimized parameters of the predictive adapted radiation therapy plan for 10% shrinkage as the initial parameter values for the optimization, and so forth to generate each of the 30%, 50%, and 80% shrinkage predictive adapted radiation therapy plans. If additional predictive adapted radiation therapy plans are to be generated for varying percentages of tumor growth, these can similarly be generated starting from the smallest percentage growth using the parameters of the base radiation therapy plan as initial parameter values, and working upward toward larger tumor growth percentages.

Similar approaches can be used to generate radiation therapy plans that accommodate various combinations of foreseeable changes. For example, radiation therapy plans can be generated for various foreseeable combinations of (i) different percentages of tumor growth or shrinkage and (ii) different levels of bladder fillage. The optional approach of generating later plans using an earlier-generated plan as an initial condition or starting point as can be utilized for such combinations of foreseeable changes. Taking the previous example, the 10%, 30%, 50%, and 80% tumor shrinkage plans can be used as starting points or initial conditions for generating additional plans encompassing different levels of bladder fillage at that tumor shrinkage percentage.

Figure 3:
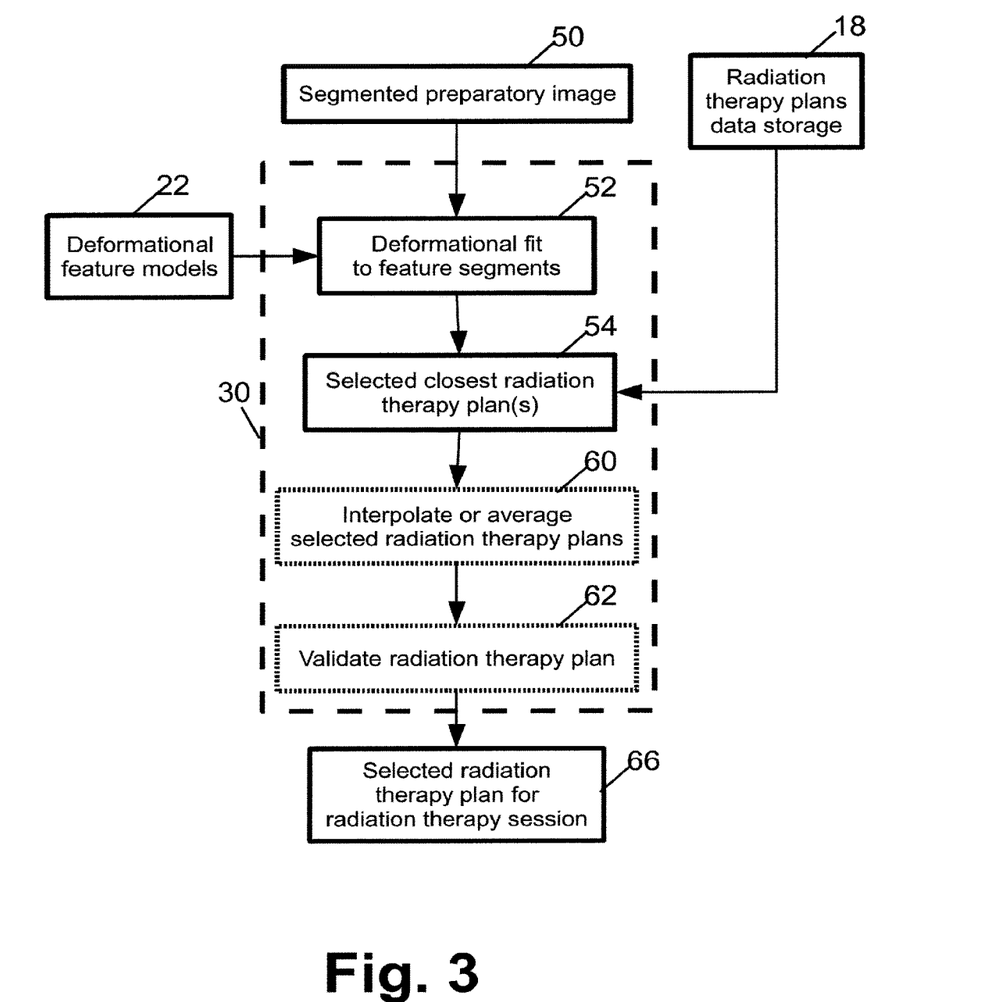
FIG. 3 diagrammatically shows a method for selecting a most appropriate radiation therapy plan for a given radiation therapy session using the system of FIG. 1.

With reference to FIG. 3, operation of the radiation therapy plan selector 30 is further described. In this embodiment, the radiation therapy plan selector 30 is assumed to operate on a segmented preparatory image 50 that has been segmented by the features segmentor 14 to identify up-to-date segments delineating the target feature to be irradiated and the one or more critical features affecting radiation transmission or whose radiation exposure is to be constrained or limited. The radiation therapy plan selector 30 suitably applies a deformational fit to feature segments, optionally utilizing the deformational feature models 22, so as to identify anatomical changes in a process operation 52. Although not illustrated, changes in tissue density (corresponding to changes in radiation attenuation or absorption by the tissue) can also be detected by comparing grayscale levels of the voxels of a segment in the segmented preparatory and planning images 40, 50. Functional changes can be detected using PET or another modality capable of providing functional information. A selection operation 54 then selects the most appropriate radiation therapy plan from the radiation therapy plans data storage 18. Optionally, the selection operation 54 may select more than one most appropriate radiation therapy plan. For example, in the previous example in which predictive radiation therapy plans are available for tumor shrinkages of 10%, 30%, 50%, and 80%, if the up-to-date segmentation of the tumor indicates a 40% shrinkage then the selection operation 54 may suitably select the predictive radiation therapy plans corresponding to 30% shrinkage and to 50% shrinkage. In such embodiments, an interpolation or averaging process 60 (indicated in phantom in FIG. 3 to show this optional operation) suitably interpolates or averages the parameter values of the 30% shrinkage and 50% shrinkage radiation therapy plans to generate an interpolated predictive radiation therapy plan that best matches the up-to-date value of 40% shrinkage. As a further option, a validation operation 62 may be performed on the interpolated predictive radiation therapy plan to ensure that the interpolation did not result in an impermissible increase in radiation exposure to a sensitive critical feature, or an impermissible decrease in radiation dosage delivered to the target feature, or so forth. The output is a selected radiation therapy plan 66 for use in the radiation therapy session.

In fractionated radiation therapy, the processing performed by the radiation therapy plan selector 30 as diagrammatically depicted in FIG. 3 is repeated prior to a predetermined number of radiation therapy sessions of the fractionated radiation therapy. As a result, the selected radiation therapy plan 66 is generally different for the different radiation therapy sessions. By "generally different", it is meant that the selected radiation therapy plan 66 is typically different for each successive radiation therapy session (for example, as the tumor gradually shinks from session to session different predictive adapted radiation therapy plans will generally be selected), but in some instances the same plan may be selected for two or more different radiation therapy sessions (for example, between two successive radiation therapy sessions the tumor shrinkage may be negligible such that the same radiation therapy plan may be selected for both of the two successive radiation therapy sessions).

The illustrated embodiments relate to radiation therapy procedures and radiation therapy planning. However, the disclosed techniques can also be used for other interventional procedures and planning, such as high intensity focused ultrasound (HIFU) procedures and HIFU planning, brachytherapy, ablation procedures, or so forth.

The illustrative example is a fractionated or multi-session therapy procedure. However, the disclosed techniques can also be used in single-session radiation therapy or other single-session therapy procedures in which a time interval separates acquisition of the therapy planning images and performance of the therapy procedure in accordance with a plan generated from the therapy planning images. The techniques disclosed herein can be used in single-session therapy procedures to generate a plurality of therapy plans encompassing various foreseeable changes that may occur between the imaging and performance of the procedure.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A radiation therapy planning device comprising:
   a computer programmed to implement:
      a radiation therapy planner configured to construct a radiation therapy plan based on a planning image segmented into segments delineating features of a subject including a tumor to be irradiated by radiation therapy and one or more critical organs whose radiation exposure during the radiation therapy is to be constrained or limited; and
      a predictive plan adaptation module configured to employ a deformational feature model to adjust the geometry of at least one of the segments to represent a foreseeable change in the subject and to invoke the radiation therapy planner to construct a radiation therapy plan corresponding to the foreseeable change; and
   a data storage configured to store a plurality of radiation therapy plans generated for a subject by the radiation therapy planner and the predictive plan adaptation module based on the planning image of the subject.

2. The radiation therapy planning device as set forth in claim 1 wherein the computer is further programmed to implement:
   a radiation therapy plan selector configured to select one of the plurality of radiation therapy plans for use in a radiation therapy session based on subject information acquired after acquisition of the planning image and before commencement of the radiation therapy session.

3. The radiation therapy planning device as set forth in claim 2 wherein the radiation therapy plan selector is configured to select one of the plurality of radiation therapy plans for use in the radiation therapy session based on a preparatory image acquired after acquisition of the planning image and before commencement of the radiation therapy session that is segmented into up-to-date segments delineating up-to-date features of the subject.

4. The radiation therapy planning device as set forth in claim 2 wherein the foreseeable change in the subject includes change in a bladder size and the radiation therapy plan selector is configured to select one of the plurality of radiation therapy plans for use in the radiation therapy session based on a fluid retention measurement of the subject performed after acquisition of the planning image and before commencement of the radiation therapy session.

5. The radiation therapy planning device as set forth in claim 2 wherein the foreseeable change in the subject includes necrosis of the tumor, the predictive plan adaptation module is configured to employ the deformational feature model to adjust the geometry of the tumor to exclude a necrotized portion of the tumor, and the radiation therapy plan selector is configured to select one of the plurality of radiation therapy plans for use in the radiation therapy session based on functional imaging of the subject.

6. The radiation therapy planning device as set forth in claim 1 wherein the foreseeable change in the subject includes translation of one of the one or more critical organs.

7. The radiation therapy planning device as set forth in claim 1 wherein the foreseeable change in the subject includes rotation of one of the one or more critical organs.

8. A radiation therapy device comprising:
   a radiation therapy planning device as set forth in claim 1 wherein the computer is further programmed to implement:
      a radiation therapy plan selector configured to select one of the plurality of radiation therapy plans for use in a radiation therapy session based on subject information acquired after acquisition of the planning image and before commencement of the radiation therapy session; and
   a radiation therapy device configured to perform the radiation therapy session by delivering radiation therapy to the subject in accord with the selected one of the plurality of radiation therapy plans.

9. A radiation therapy planning device for planning a fractionated radiation therapy, the radiation therapy planning device comprising:
   a computer programmed to:
      generate a plurality of radiation therapy plans by operations including:
         segmenting a planning image into segments delineating features of a subject including a tumor to be irradiated by the fractionated radiation therapy and one or more critical organs whose radiation exposure during the fractionated radiation therapy is to be constrained or limited;
         constructing a radiation therapy plan based on the planning image segmented into said segments delineating features of the subject; and
         deforming at least one of the segments to represent a foreseeable change in the subject and repeating the constructing with the deformation to construct a radiation therapy plan corresponding to the foreseeable change; and
      select one of the plurality of radiation therapy plans for use in a radiation therapy session of the fractionated radiation therapy based on subject information acquired after acquisition of the planning image and before commencement of the radiation therapy session.

10. The radiation therapy planning device as set forth in claim 9 wherein the computer is further programmed to select the one of the plurality of radiation plans by:
    segmenting a preparatory image acquired after acquisition of the planning image and before commencement of the radiation therapy session into up-to-date segments delineating up-to-date features of the subject; and
    selecting said one of the plurality of radiation therapy plans for use in the radiation therapy session based on the preparatory image segmented into said up-to-date segments.

11. The radiation therapy planning device as set forth in claim 9 wherein the foreseeable change in the subject includes change in a bladder size and the selecting comprises:
    selecting said one of the plurality of radiation therapy plans for use in the radiation therapy session based on a fluid retention measurement of the subject performed after acquisition of the planning image and before commencement of the radiation therapy session.

12. The radiation therapy planning device as set forth in claim 9 wherein:
    the foreseeable change in the subject includes necrosis of the tumor;
    the deforming comprises deforming one or more segments delineating the tumor to exclude a necrotized portion of the tumor; and
    the computer is further programmed to select the one of the plurality of radiation plans by:
       selecting said one of the plurality of radiation therapy plans for use in the radiation therapy session based on a functional image of the subject acquired after acquisition of the planning image and before commencement of the radiation therapy session.

13. The radiation therapy planning device as set forth in claim 9 wherein the foreseeable change in the subject includes translation of one of the one or more critical organs.

14. The radiation therapy planning device as set forth in claim 9 wherein the foreseeable change in the subject includes rotation of one of the one or more critical organs.

15. A radiation therapy device comprising:
a radiation therapy planning device as set forth in claim 9; and
a radiation therapy device configured to perform the radiation therapy session of the fractionated radiation therapy in accord with the selected one of the plurality of radiation therapy plans.

16. A radiation therapy planning device for planning a fractionated radiation therapy, the radiation therapy planning device comprising:
a computer programmed to:
generate a plurality of radiation therapy plans by operations including constructing a radiation therapy plan based on a planning image segmented into segments delineating features of a subject and performing one or more iterations of:
adjusting the segmented planning image to represent a foreseeable change in the subject including at least one of: change in a bladder size, necrosis of a tumor, translation of a critical organ, and rotation of a critical organ; and
constructing a radiation therapy plan corresponding to the foreseeable change based on the adjusted segmented planning image representing the foreseeable change; and
select one of the plurality of radiation therapy plans for use in a radiation therapy session of the fractionated radiation therapy based on subject information acquired after acquisition of the planning image and before commencement of the radiation therapy session.

17. The radiation therapy planning device as set forth in claim 16 wherein the performing one or more iterations includes performing an iteration of:
adjusting the segmented planning image to represent change in a bladder size; and
constructing a radiation therapy plan corresponding to the change in the bladder size based on the adjusted segmented planning image representing the change in the bladder size.

18. The radiation therapy planning device as set forth in claim 16 wherein the performing one or more iterations includes performing an iteration of:
adjusting the segmented planning image to represent necrosis of the tumor by adjusting one or more segments delineating the tumor to exclude a necrotized portion of the tumor; and
constructing a radiation therapy plan corresponding to necrosis of the tumor based on the adjusted segmented planning image representing the necrosis of the tumor.

19. The radiation therapy planning device as set forth in claim 16 wherein the performing one or more iterations includes performing an iteration of:
adjusting the segmented planning image to represent movement of the critical organ comprising at least one of translation and rotation; and
constructing a radiation therapy plan corresponding to the movement of the critical organ based on the adjusted segmented planning image representing the movement of the critical organ.

20. A radiation therapy device comprising:
a radiation therapy planning device as set forth in claim 16; and
a radiation therapy device configured to perform the radiation therapy session of the fractionated radiation therapy in accord with the selected one of the plurality of radiation therapy plans.

* * * * *